United States Patent
Meudt et al.

(10) Patent No.: US 6,265,607 B1
(45) Date of Patent: Jul. 24, 2001

(54) PROCESS FOR THE PREPARATION OF 4-(4'-CHLOROBIPHENYL-4-YL)-4-KETO-2-METHYLENEBUTYRIC ACID

(75) Inventors: Andreas Meudt, Floersheim-Weilbach; Wilfried Pressler, Kelkheim; Antje Noerenberg, Buettelborn; Steffen Haber, Königstein; Michael Erbes, Frankfurt; Robert Cosmo, Darmstadt, all of (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/366,472

(22) Filed: Aug. 3, 1999

(30) Foreign Application Priority Data

Aug. 5, 1998 (DE) .............................. 198 35 359

(51) Int. Cl.⁷ .................................................. C07L 59/74
(52) U.S. Cl. ............................................................ 562/459
(58) Field of Search .............................................. 562/459

(56) References Cited

U.S. PATENT DOCUMENTS

| | | |
|---|---|---|
| 4,008,323 | 2/1977 | Cousse et al. . |
| 4,058,558 | 11/1977 | Cousse et al. . |
| 5,789,434 | 8/1998 | Kluender et al. . |

FOREIGN PATENT DOCUMENTS 25 13 157   10/1975   (DE) .

2513157   10/1975   (DE) .

OTHER PUBLICATIONS

"Snythèse structure et activitè hypocholestèrolèmiante d'une sèrie d'acides γ–aryl, γ–oxo butyriques substituès et dèrivès" H. Cousse, G. Mouzin, J. Rieu, A. Delhon, F. Bruniquel, F. Fauran, Eur. J. Med. Chem. 22, (1987), pp. 45–57.

"Secondary Products of Itanoxone," J. Rieu, G. Mouzin, H. Cousse, and A. Boucherle, Journal of Pharmaceutical Sciences, vol. 69, No. 1, Jan. 1980, pp. 49–53.

*Primary Examiner*—Paul J. Killos
(74) *Attorney, Agent, or Firm*—Scott E. Hanf

(57) ABSTRACT

The invention relates to a process for the preparation of 4-(4'-chlorobiphenyl-4-yl)-4-keto-2-methylenebutyric acid of the formula (I)

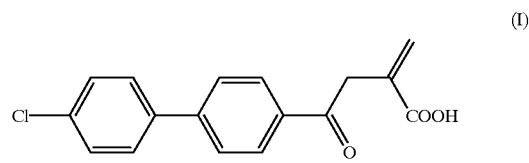

(I)

by Friedel-Crafts acylation of 4-chlorbiphenly with itaconic anhydride, which comprises carrying out the Friedel-Crafts acylation in aromatic solvents at a temperature from −20 to +80° C.

15 Claims, No Drawings

PROCESS FOR THE PREPARATION OF 4-(4'-CHLOROBIPHENYL-4-YL)-4-KETO-2-METHYLENEBUTYRIC ACID

CROSS-REFERENCE TO RELATED APPLICATION

The present invention is described in the German priority application No. 19835359.6, filed Aug. 5, 1998, which is hereby incorporated by reference as is fully disclosed herein.

BACKGROUND OF THE INVENTION

The invention relates to a novel process for the preparation of 4-(4'-chlorobiphenyl-4-yl)-4-keto-2-methylenebutyric acid of the formula (I) below.

4-(4'-Chlorobiphenyl-4-yl)-4-keto-2-methylenebutyric acid is an important intermediate for the synthesis of matrix metalloendoproteinase inhibitors (MMP), which are employed as active compounds for the prevention of the metastasis of malignant tumors. The compound, however, is prone to isomerization to give conjugated isomers. This reaction is induced by traces of base, strong acids and thermal stress.

On account of the importance of 4-(4'-chlorobiphenyl-4-yl)-4-keto-2-methylenebutyric acid of the formula (I), a large number of procedures for the preparation of this compound exist. All known syntheses of the compound start from 4-chlorobiphenyl of the formula (II), which is reacted with $AlCl_3$ and itaconic anhydride of the formula (III).

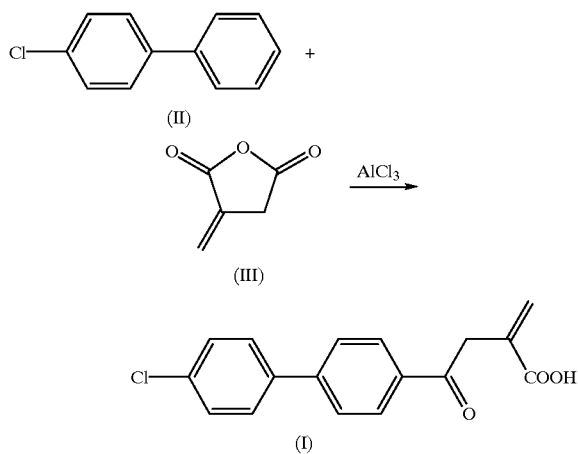

J.-P. Rieu et al. (J. Pharm. Sci. 1980, 69, 49) carry out the reaction in the solvent dichloromethane. After aqueous work-up, removal of the solvent by distillation and recrystallization from an 11-fold volume of ethyl acetate, the product is obtained in a yield of only 52%.

H. Cousse et al. (Eur. J. Med. Chem. 1987, 22, 45–57) use 1,2-dichloroethane or dichloromethane as a solvent. After aqueous work-up, the organic phase is mixed with ethanol and acetone, whereupon the product precipitates, and is filtered off with suction and recrystallized. The yields indicated are, however, only 46%.

In DE-A-25 13 157 too, biphenyls and halobiphenyls are acylated with itaconic anhydride according to Friedel-Crafts in the presence of a Lewis acid catalyst. The solvent used here is the strongly toxic 1,1,2,2-tetrachloroethane. Yields for the acylation of 4-chlorobiphenyl are not indicated.

SUMMARY OF THE INVENTION

The invention was based on the object of providing a process for the preparation of 4-(4'-chlorobiphenyl-4-yl)-4-keto-2-methylenebutyric acid which can be carried out industrially, which avoids the highly toxic chlorinated aliphatic hydrocarbons mentioned and affords the target product in good yields. Moreover, the process to be developed should be as free as possible of technically complicated purification procedures such as recrystallization or chromatography.

Surprisingly, it has been found that the acylation of 4-chlorobiphenyl with itaconic anhydride under catalysis with $AlCl_3$ in aromatic solvents leads to 4-(4'-chlorobiphenyl-4-yl)-4-keto-2-methylenebutyric acid in very good yields. In spite of the already mentioned high lability, the target product is surprisingly obtained in very high purity. It is furthermore surprising that under the conditions according to the invention no acylation of the solvent is observed.

DESCRIPTION OF THE PREFERRED EMBODIMENTS

The present invention therefore relates to a process for the preparation of 4-(4'-chlorobiphenyl-4-yl)-4-keto-2-methylenebutyric acid of the formula (I)

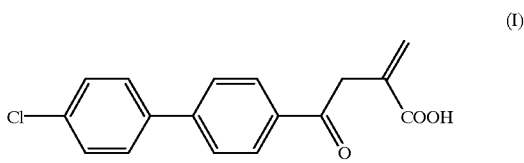

by Friedel-Crafts acylation of 4-chlorobiphenyl with itaconic anhydride, which comprises carrying out the Friedel-Crafts acylation in aromatic solvents at a temperature from −20 to +80° C.

Suitable aromatic solvents are preferably those which, under the conditions according to the invention, are acylated significantly more slowly than 4-chlorobiphenyl, for example benzonitrile, nitrobenzene, bromo- and chloroaromatics. o-Dichlorobenzene, chlorobenzene and p-chlorotoluene are particularly preferred. Mixtures of these solvents can also be employed.

The starting materials 4-chlorobiphenyl and itaconic anhydride are expediently reacted in a molar ratio of 0.8:1 to 1.2:1, preferably 0.9:1 to 1.1:1.

The Friedel-Crafts catalyst employed is, for example, $AlCl_3$. The amount of Friedel-Crafts catalyst is expediently 1.0 to 5 mol per mole of itaconic anhydride, preferably 2.01 to 2.7 mol per mole of itaconic anhydride.

In a preferred embodiment, 4-chlorobiphenyl and itaconic anhydride are dissolved in the solvent and this solution is added to a suspension of the Friedel-Crafts catalyst in the solvent, expediently at a temperature of −20 to +80° C., preferably at −10 to +55° C., particularly preferably at −0 to 45° C.

It is also possible to meter in a solid mixture of the reactants mentioned into initially introduced solvent. It is also possible to add the reactants separately in solid form. The addition time or dropwise-addition time can be between 1 minute and 12 hours, preferably between 0.5 and 4 hours.

The amount of solvent used (total of solvent in the recipient vessel and the solvent used for the dissolution of the reactants) can be varied within a wide range, as well as the ratio of the amounts of solvent in the recipient vessel to give the amount of solvent which is used for the dissolution of the starting materials. Total amounts of solvent between 0.5 and 20 parts by weight per part by weight of 4-chlorobiphenyl, preferably between 8 and 16, particularly preferably between 11 and 15, parts by weight per part by weight of 4-chlorobiphenyl, are expedient.

After completion of the dropwise addition or the addition, the reaction mixture is stirred for 0.5 to 24 hours, preferably 1 to 6 hours, preferably at temperatures from 0 to 55° C.

It is then hydrolyzed with water, dilute aqueous hydrochloric acid or dilute aqueous sulfuric acid.

The hydrolysis is expediently carried out by introducing the reaction mixture into water, hydrochloric acid or sulfuric acid, which are preferably 0 to 35% strength by weight, temperatures between 0 and 80° C. being preferred. The aqueous phase is separated off and the organic phase is washed one or more times with dilute hydrochloric acid or sulfuric acid (0 to 35% strength by weight). The product present suspended in the solvent is filtered off and washed one or more times with suitable solvents and dried. Suitable solvents are those which, compared with the reaction product, behave in an inert manner and have a solubility for the product of below 5%, for example o-dichlorobenzene, chlorobenzene, ethanol or ethanol-water mixtures.

In general, almost quantitative reactions to give the desired product are achieved.

It is furthermore advantageous to wash the mother liquor with a solution of a suitable complexing agent, for example a multidentate complexing agent such as ethylenediaminetetraacetic acid, it being possible for aluminum which may be contained in the product to be complexed and an isomerization of the product to give conjugated isomers to be prevented. The mother liquor can be concentrated, whereby the yield can be further increased.

The 4-(4'-chlorobiphenyl-4-yl)-4-keto-2-methylenebutyric acid thus obtained is subjected to drying. The drying of the product can be carried out at temperatures between 20° C. and 110° C. under pressures between normal pressure and 1 mbar.

EXAMPLES

The following examples are intended to illustrate the invention without restricting it.

Example 1

212 g (1.59 mol) of anhydrous aluminum chloride are introduced into 1200 g of o-dichlorobenzene and brought to 45° C. with stirring. A solution of 78.5 g (0.7 mol) of itaconic anhydride and 132 g (0.7 mol) of 4-chlorobiphenyl in 600 g of o-dichlorobenzene at 45° C. is added dropwise in the course of one hour. The reaction mixture is stirred at 45° C. for one hour and then added to an ice-cold mixture of 1000 g of water and 142 g of hydrochloric acid (37%). The aqueous phase is separated off. The organic phase is washed three times with a mixture of 1000 g of water and 50 g of hydrochloric acid (37%) in each case. After washing three times, it is allowed to cool to approximately 20° C. and the colorless product is then filtered off with suction. This is then washed twice with 200 g of o-dichlorobenzene in each case. The product is dried at 40° C. and about 100 mbar until it is free of solvent and water. 150 g (0.50 mol) of 4-(4'-chlorobiphenyl-4-yl)-4-keto-2-methylenebutyric acid (71%) are obtained as a colorless, finely crystalline powder. Further product can be obtained by working up the mother liquor. The dichlorobenzene phase is washed a number of times with 0.1% strength by weight aqueous EDTA solution. After distilling off the dichlorobenzene in vacuo, further product is obtained by cooling the residue to 0° C., filtering off the colorless precipitate with suction and recrystallizing the residue, and the yield is increased to >85%. (HPLC purity 99.3–99.6%).

Example 2

212 g (1.59 mol) of anhydrous aluminum chloride are introduced into 1800 g of o-dichlorobenzene and the mixture is brought to 45° C. with stirring. A solid mixture of 78.5 g (0.7 mol) of itaconic anhydride and 132 g (0.7 mol) of 4-chlorobiphenyl is added in the course of one hour. The reaction mixture is stirred at 45° C. for two hours and then added to an ice-cold mixture of 900 g of water and 100 g of hydrochloric acid (37%). The aqueous phase is separated off. The organic phase is washed three times with a mixture of 1000 g of water and 25 g of hydrochloric acid (37%) in each case. After washing three times, it is allowed to cool to approximately 20° C. and the colorless product is then filtered off with suction. This is then washed twice with 150 g of ethanol/water 90:10 in each case. The product is dried at 80° C. and about 110 mbar until free of solvent and water. 148 g (0.49 mol) of 4-(4'-chlorobiphenyl-4-yl)-4-keto-2-methylenebutyric acid (70%) are obtained as a colorless, finely crystalline powder. By working up the mother liquor, as described in Example 1, the yield is increased to 87%. (HPLC purity 99.3–99.5%).

Example 3

193.3 g (1.45 mol) of anhydrous aluminum chloride are introduced in 1100 g of o-dichlorobenzene and the mixture is brought to 45° C. with stirring. A solution of 80.9 g (0.72 mol) of itaconic anhydride and 132 g (0.7 mol) of 4-chlorobiphenyl in 700 g of o-dichlorobenzene at 50° C. is added dropwise in the course of three hours. The reaction mixture is stirred at 25° C. for four hours and then added to an ice-cold mixture of 1000 g of water and 25 g of sulfuric acid (96%). The aqueous phase is separated off. The organic phase is washed three times with a mixture of 1000 g of water and 15 g of sulfuric acid (96%) in each case. After washing three times, it is allowed to cool to approximately 20° C. and the colorless product is then filtered off with suction. This is then washed three times with 150 g of ethanol (96%) in each case. The product is dried at 60° C. and about 100 mbar until free of solvent and water. 148 g (0.49 mol) of 4-(4'-chlorobiphenyl-4-yl)-4-keto-2-methylenebutyric acid (70%) are obtained as a colorless, finely crystalline powder. By working up the mother liquor, as described in Example 1, the yield is increased to 83%. (HPLC purity 99.6–99.8%)

Example 4

21.2 g of anhydrous aluminum chloride are introduced into 130 g of chlorobenzene and the mixture is cooled to 0° C. A solid mixture of 8.3 g of itaconic anhydride and 13.2 g of 4-chlorobiphenyl is added in portions in the course of one hour. The reaction mixture is stirred at 0° C. for three hours and then added to ice water. The solid reaction product is filtered off and washed twice with water (50 ml). The product is dried at room temperature and about 100 mbar until free of solvent and water. 4-(4'-Chlorobiphenyl-4-yl)-4-keto-2-methylenebutyric acid is obtained in a yield of 75% as a colorless, finely crystalline powder.

Example 5

21.2 g of anhydrous aluminum chloride are introduced into 50 g of bromobenzene and the mixture is cooled to 0° C. A solid mixture of 8.3 g of itaconic anhydride and 13.2 g of 4-chlorobiphenyl is added in portions in the course of one hour. The reaction mixture is stirred at 0° C. for two hours and then added to 100 g of ice water. The solid reaction product is filtered off and washed twice with water (50 ml). After recrystallization from ethyl acetate, the product is dried at room temperature and about 100 mbar until free of solvent and water. 4-(4'-Chlorobiphenyl-4-yl)-4-keto-2-methylenebutyric acid is obtained in a yield of 50% as a colorless, finely crystalline powder.

Example 6

21.2 g of anhydrous aluminum chloride are introduced into 50 g of p-chlorotoluene and the mixture is heated to 40° C. with stirring. A solid mixture of 8.3 g of itaconic anhydride and 13.2 g of 4-chlorobiphenyl is added in portions in the course of one hour. The reaction mixture is stirred at 40° C. for 30 minutes and then added to 100 g of ice water. The solid reaction product is filtered off and washed twice with water (50 ml). The product is dried at room temperature and about 100 mbar until free of solvent and water. 4-(4'-Chlorobiphenyl-4-yl)-4-keto-2-methylenebutyric acid is obtained in a yield of 70% as a colorless, finely crystalline powder.

What is claimed is:

1. A process for the preparation of 4-(4'-chlorobiphenyl-4-yl)-4-keto-2-methylenebutyric acid of the formula (I)

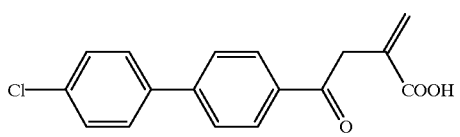

by Friedel-Crafts acylation of 4-chlorobiphenyl with itaconic anhydride, which comprises carrying out the Friedel-Crafts acylation in aromatic solvents at a temperature from −20 to +80° C.

2. The process as claimed in claim 1, wherein the aromatic solvent is one which under the process conditions is acylated significantly more slowly than 4-chlorobiphenyl.

3. The process as claimed in claim 1, wherein the aromatic solvent is a bromoaromatic, a chloroaromtic, benzonitrile or nitrobenzene.

4. The process as claimed in claim 1, wherein the aromatic solvent is o-dichlorobenzene, chlorobenzene or p-chlorotoluene.

5. The process as claimed in claim 1, wherein $AlCl_3$ is employed as a Friedel-Crafts catalyst.

6. The process as claimed in claim 1, wherein, after the Friedel-Crafts acylation, hydrolysis with water, aqueous, hydrochloric acid or aqueous sulfuric acid is carried out.

7. The process as claimed in claim 1, wherein 4-chlorobiphenyl and itaconic acid are dissolved in the aromatic solvent and this solution is added to a suspension of the Friedel-Crafts catalyst in the aromatic solvent.

8. The process as claimed in claim 1, wherein 4-chlorobiphenyl and itaconic anhydride are added in solid form to a suspension of the Friedel-Crafts catalyst in the aromatic solvent.

9. The process as claimed in claim 7, wherein the addition time is between 1 minute and 12 hours.

10. The process as claimed in claim 8, wherein the addition time is between 1 minutes and 12 hours.

11. The process as claimed in claim 9, wherein after completion of the addition stirring is carried out for 0.5 to 24 hours at a temperature between 0 and 55° C.

12. The process as claimed in claim 10, wherein after completion of the addition stirring is carried out for 0.5 to 24 hours at a temperature between 0 and 55° C.

13. The process as claimed in claim 1, wherein the product present suspended in the solvent after the hydrolysis is filtered off.

14. The process as claimed in claim 13, wherein the mother liquor remaining after the filtration is washed with a solution of a multidentate complexing agent.

15. The process as claimed in claim 14, herein the mother liquor washed with a solution of a multidentate complexing agent is concentrated and the product present suspended in the solvent is filtered off.

* * * * *